United States Patent [19]

Kompelien

[11] Patent Number: 4,465,229
[45] Date of Patent: Aug. 14, 1984

[54] HUMIDITY COMFORT OFFSET CIRCUIT

[75] Inventor: Arlon D. Kompelien, Richfield, Minn.

[73] Assignee: Honeywell, Inc., Minneapolis, Minn.

[21] Appl. No.: 436,742

[22] Filed: Oct. 25, 1982

[51] Int. Cl.³ .................. F24F 11/00; F25D 11/04
[52] U.S. Cl. .................. 236/44 E; 62/176.6; 73/336.5; 374/142
[58] Field of Search .................. 62/176 E, 209; 236/44 E, 44 R, 44 C; 374/142; 73/336.5

[56] References Cited

U.S. PATENT DOCUMENTS

| | | |
|---|---|---|
| 2,171,803 | 9/1939 | Parks et al. . |
| 2,949,513 | 8/1960 | Davidson . |
| 3,046,411 | 7/1962 | Steiner .................. 236/44 E |
| 3,080,465 | 3/1963 | Pelishek . |
| 3,118,601 | 1/1964 | Robb, Jr. .................. 236/44 E |
| 3,181,791 | 5/1965 | Axelrod .................. 236/44 L |
| 3,182,222 | 5/1965 | Lacy et al. .................. 236/44 R |
| 3,188,553 | 6/1965 | Eurenius .................. 236/44 R |
| 3,599,862 | 8/1971 | Hogan et al. . |
| 3,730,426 | 5/1973 | Braukmann . |
| 3,859,616 | 1/1975 | Ladany . |
| 3,936,793 | 2/1976 | Armstrong . |
| 3,949,607 | 4/1976 | Nodolf . |
| 3,970,246 | 7/1976 | Attridge, Jr. et al. . |
| 3,999,706 | 12/1976 | Lewis . |
| 4,105,063 | 8/1978 | Bergt . |
| 4,319,485 | 3/1982 | Terada et al. . |

Primary Examiner—William E. Wayner
Attorney, Agent, or Firm—Alfred N. Feldman

[57] ABSTRACT

A humidity responsive circuit is adapted to be connected to a thermostat to provide a humidity comfort offset to the thermostat. The humidity comfort offset circuit can be added to a retrofit item or could be added during the manufacture of an electronic thermostat which has a bridge in its input for measuring the temperature. The humidity comfort offset circuit have an output range with at least one humidity value being equal to the balance value of the bridge.

8 Claims, 1 Drawing Figure

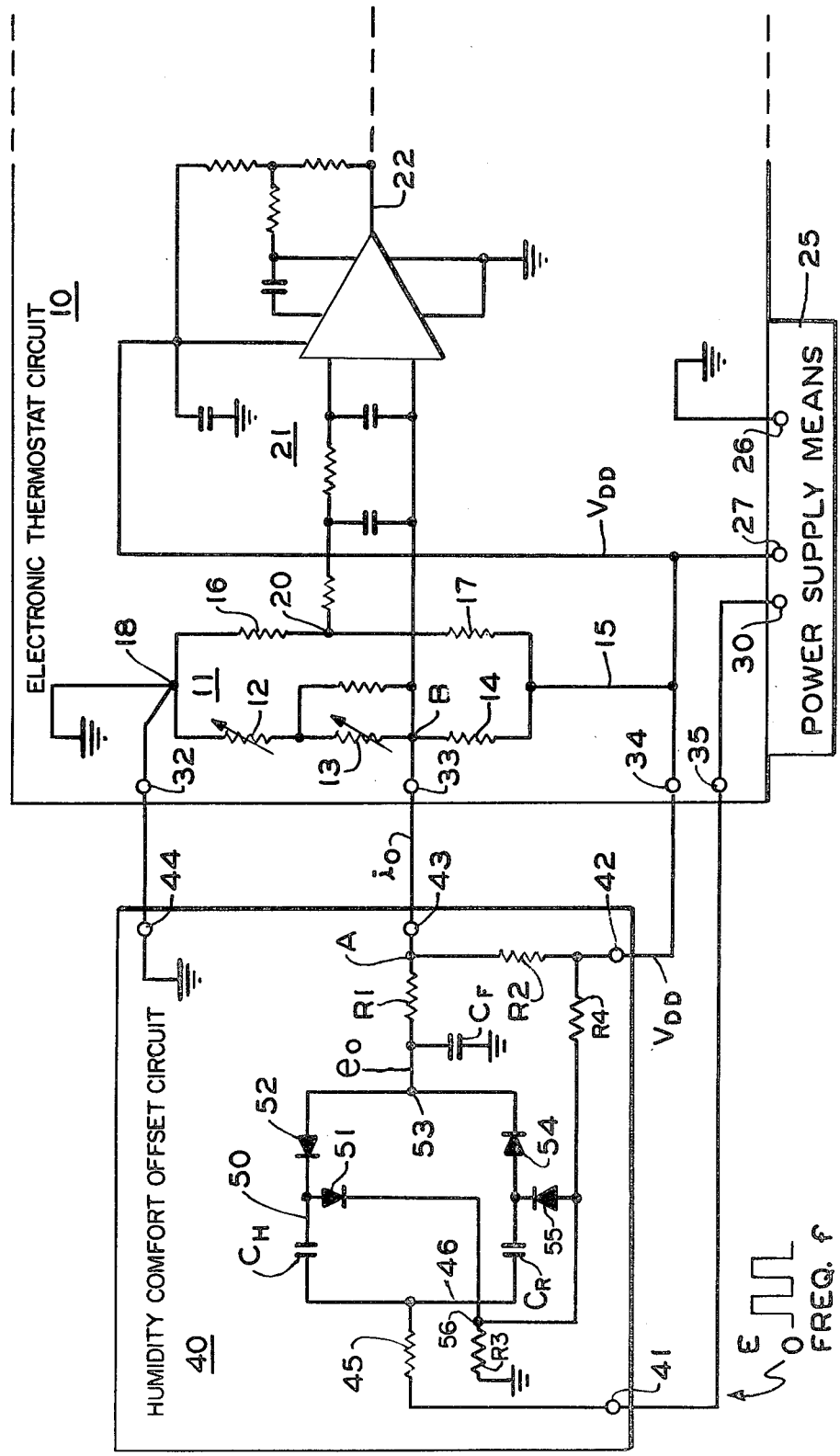

HUMIDITY COMFORT OFFSET CIRCUIT

BACKGROUND OF THE INVENTION

It has long been recognized in the temperature control art that the level of humidity can be correlated with the degree of comfort at any particular temperature. In the control of indoor temperatures, it has been common to add humidity to the air during the winter heating season, and to try to remove humidity during the summer cooling season. Despite the fact that the interrelationship between humidity and temperature is well recognized, it has not been a common practice to try to control humidity directly with temperature to maintain a particular level of comfort.

By and large, most thermostats are electromechanical or mechanical in structure, and it has been very difficult to measure humidity. There has been some attempt to mechanically interlink a humidity control with a temperature control, but this type of device is rather expensive, complex, and is not susceptible of retrofit once a thermostat has been manufactured and/or installed. For the most part, humidity has been controlled totally independent of the temperature control and usually is set at some range dependent on outdoor temperatures. Typically, if humidity control is added to a thermostatically controlled system, it is as a modification of the output of the thermostat control system.

SUMMARY OF THE INVENTION

The present invention is directed to a humidity comfort offset control circuit that forms part of an input to an electronic thermostat which has a bridge or similar input circuit for measuring and controlling temperature. The present invention can be provided as an integral part of a thermostat, or can be provided as an add-on feature to an electronic thermostat that can be conveniently added, after the manufacture and/or installation of the thermostat.

The present humidity comfort offset control circuit provides an output control signal that is matched to the bridge or temperature measuring system of an electronic type of thermostat. The electronic thermostat has of recent years become the dominant type of approach in temperature control, as the utilization of electronics and microprocessors has allowed for sophisticated temperature control with respect to time and other conditions. In this type of thermostat it is possible to match a humidity sensitive control circuit so that the humidity comfort control circuit can be added either during the original manufacturing process or can be retrofitted to provide an offset to the electronic thermostat in response to the humidity conditions thereby maintaining a constant level of comfort even if the humidity in a location changes.

BRIEF DESCRIPTION OF THE DRAWING

The single FIGURE discloses a schematic of a humidity comfort offset circuit adapted to be connected into an electronic thermostat.

DESCRIPTION OF THE PREFERRED EMBODIMENT

A thermostat is partially shown at 10 and is disclosed as an electronic thermostat. The thermostat 10 has a bridge circuit 11 including a setpoint potentiometer 12 and a sensing thermistor or temperature responsive resistor 13. The resistor 13 is connected at a node B to a further resistor 14 that in turn is connected by a conductor 15 to a source of power identified as $V_{DD}$. The bridge 11 is completed by resistors 16 and 17 to form a conventional Wheatstone bridge arrangement in which a setpoint can be entered by an adjustment of the resistor 12. In order for the bridge to be balanced or unbalanced in response to a temperature, the temperature responsive resistor 13 is provided. The bridge has an output at node 20 with respect to the node B. The bridge 11 is grounded at 18. The bridge 11 in turn controls amplifying circuit means generally disclosed at 21 that has an output at 22 to control a heating and/or load.

The thermostat 10 is supplied with electrical power and can have an internal or supplemental power supply means. The power supply means has been disclosed at 25 as a supplemental power supply means merely as a way of identifying the source of power for the thermostat 10, and for the novel circuitry that will be described later in the present text. The power supply means 25 is grounded at terminal 26 and has an output voltage $V_{DD}$ at terminal 27 which is connected to the conductor 15. The power supply means 25 has a further output at terminal 30. The output at terminal 30 is disclosed as a square wave type of alternating current drive voltage that varies from zero volts to a voltage level E at a frequency f. This frequency power output is usually available from the time keeping circuit of an energy savings thermostat.

The thermostat 10 is disclosed as including a series of terminal means 32, 33, 34, and 35 for connection to a humidity responsive circuit means generally disclosed at 40. The humidity responsive circuit 40 can be an add-on circuit to the thermostat 10 (as is schematically shown), or could be obviously included directly as part of the electronics of the thermostat 10. The humidity comfort offset circuit 40 includes a series of terminals 41, 42, 43, and 44 that interconnect the humidity comfort offset circuit 40, to the power supply means 25 and the thermostat 10. The terminal 44 is a ground terminal connected to terminal 32. The terminal 43 is an output terminal for the humidity comfort offset circuit 40 and is connected to the terminal 33 which in turn is directly connected to the node B of the thermostat bridge. The terminal 42 is connected to the terminal 34 which is a source of operating potential at the voltage $V_{DD}$. The terminal 41 is connected to the terminal 35 which in turn is connected to the terminal 30 of the power supply means 25 to supply an alternating current drive voltage of frequency f to the humidity comfort offset circuit 40.

The humidity comfort offset circuit 40 includes a resistor 45 that is connected to a conductor 46 that is common to a capacitor $C_H$ and a second capacitor $C_R$. The capacitor $C_H$ is a humidity responsive capacitor and could be of a polyimide capacitive type which is a high impedance type of capacitance that changes its capacitance value with changes in humidity. The capacitor $C_R$ is a reference balancing capacitor that also provides stabilization for the circuit diodes.

The capacitor $C_H$ is connected to a conductor 50 that in turn is connected to ground through a diode 51 and through a further diode 52 to a node 53 that is common to a further diode 54. The diode 54 is connected through a diode 55 to a voltage biasing node 56 of the system. The node 53 has a voltage that will be identified as $e_o$ and in turn is connected to a capacitor $C_f$ which is connected to ground. The capacitor $C_f$ is a low pass filter capacitor. The voltage $e_o$ is connected through a resistor R1 that in turn is connected to a node A which is common to the terminal means 43. The node A is further connected to a resistor R2 that is connected to the terminal 42. Voltage biasing node 56 receives its bias current through resistor R4 connected to terminal 42 and resistor R3 connected to ground to complete the circuit.

DESCRIPTION OF OPERATION

Capacitive humidity elements, such as the polyimide sensor, have recently been developed that make humidity measurement more accurate and relatively inexpensive. Work has been done in the past, reported in ASHRE Journals, etc. on the effects of humidity on comfort. Typically, the temperature setpoint should be decreased by about 0.06 degrees Fahrenheit for each percent of increase in humidity.

It is preferred that a humidity offset circuit, if added, can be added to an electronic thermostat temperature sensing and setpoint circuit without any changes to the temperature part of the circuit. As shown in the present invention, the voltage at node A of the circuit can be calibrated at a mid-humidity point such as 50% relative humidity to be equal to that of node B in the temperature control circuit of a thermostat when it is in control. Then when node A and node B are connected, no shift will occur in the setpoint. When humidity changes, a driving current $i_o$ will occur out of node A to provide the desired shift in temperature control point. The temperature circuit 10 shown here is part of that used in conventional electronic thermostats. An alternating current drive voltage is applied to the capacitive humidity sensor circuit means 40. Resistor 45 and R3 which limit peak capacitive currents from this drive voltage are sufficiently low in impedance such that the capacitive charges come to equilibrium before the end of each half cycle. Then, through two diodes, this charge change pumps current out of the $e_o$ labeled node in the circuit. To minimize effects of temperature changes in the diodes 51 and 52, and provide a direct current offsetting current, a reference capacitor $C_R$ with two other diodes 54 and 55 are added such that this capacitor pumps current into the $e_o$ node. Capacitor $C_F$ is added to limit the alternating current ripple at $e_o$. Resistor R1 is then selected such that the correct drive current change with humidity occurs out of node A. Since node B of the temperature circuit is not at 0 volts, resistor R2 is selected to bring the resultant drive current from node A to zero at the humidity value where no setpoint offset is desired. The direction of pumping current into or out of the $e_o$ node by the humidity sensor depends on the requirement of node B to shift the setpoint in the correct direction. The output driving impedance from node A must be maintained sufficiently higher than the impedance looking into node B to limit dynamic loading of the temperature signal. Equations were derived based on charge pumping equations. These are given below.

$$i_o = \frac{V_{DD} - E_B}{R_2} + \frac{f[(E - 2V_D)(C_R - C_H) - E_B(C_R + C_H)]}{1 + f(C_R + C_H)R_1}$$

and from this $$\frac{di_o}{dC_H} = \frac{-f[(E - 2V_D)(1 + 2fC_RR_1) + E_B]}{[1 + f(C_R + C_H)R_1]^2}$$

In these equations $E_B$ voltage at node B while the thermostat is in control, $V_{DD}$ is the direct current supply voltage, E is the peak to peak voltage from the alternating current drive signal, f is the frequency of the drive signal, $V_D$ is the voltage drop of a diode, $C_H$ is the capacitance of the humidity sensor, $C_R$ is the capacitance of a reference capacitor, and R1 and R2 are resistors as shown in the circuit.

From these equations it can be seen that $C_R$ should be near the nominal operating capacitance of $C_H$ to minimize the effects of temperature variations in $V_D$. Then resistor R1 is selected such that $di_o/dC_H$ is at the desired value. From the humidity element characteristic, we can get a value of $dC_H/d(\%RH)$. From the characteristics of the temperature sensing part of the circuit at node B, we can derive a value for $di_o/dT$ to offset temperature and from the comfort characteristics we get a value for $dT/d(\%RH)$. The product of these last two are $[dT/d(\%RH)] \times [di_o/dT] = di_o d(\%RH)$. Then $di_o/dC_H$ of the circuit must equal this $[di_o/d(\%RH)]$ divided by the $dC_H/d(\%RH)$ of the humidity element.

In a typical application the following values were used. $E=4.8$, $V_{DD}=5$, $f=2048$, $V_D=0.6$, $C_H=443\times10^{-12}$, $C_R=500\times10^{-12}$, $dC_H/d(\%RH)=1.03\times10^{-12}$. For the temperature circuit $E_B$ calculated $=1.2$ volts, $di_o/dT=0.0963\times10^{-6}$ and from the comfort characteristics $dT/d(\%RH)=-0.06$. From this $$\frac{di_o}{dC_H} = \frac{(-.06) \times (.0963 \times 10^{-6})}{1.03 \times 10^{-12}} = -5610$$

Applying this to the $di_o/dC_H$ equation and using a quadratic solution, a value of $R1=319,000$ ohms is derived.

Since we want a value of $i_o=0$ with $C_H=443\times10^{-12}$, R2 calculates from the $i_o$ equation to be 3,236,000 ohms. $C_F$ is chosen to limit the ripple value of the charge pump currents to a negligible value relative to the $i_o$ output current sensitivity. A 0.1 uf capacitor should be sufficient. A small impedance is added in series with the alternating current drive voltage to spread the charge current out over a portion of each half cycle.

The voltage level at the node $e_o$ could forward bias both diodes 51 and 52 at the same time and cause faulty operation. In the case disclosed, the voltage of $e_o$ is approximately equal to $$E_B - \frac{V_{DD} - E_B}{R_2} R_1$$

or 0.825 volts which could cause a bias current through diodes 51 and 52 that degrades the pumping current from $C_H$. To prevent this the bias voltage resistor divider network of R3 and R4 is set to provide approximately 0.825 volts at node 56 to eliminate the harmful bias current through diodes 51 and 52.

As can be seen from the detailed description of operation of the present humidity comfort offset circuit which is adapted to be operated with a bridge circuit of a thermostat 10, it becomes apparent that the circuit could be readily incorporated directly within the thermostat 10 or could be provided as an add-on feature. The type of humidity control circuit could be altered extensively depending on the humidity sensitive element being used, and the degree of comfort offset required. The inventor wishes to be limited in the scope of his invention solely by the scope of the appended claims.

The embodiments of the invention in which an exclusive property or right is claimed are defined as follows:

1. A humidity comfort offset circuit having output means adapted to be connected to a bridge circuit of a thermostat to adjust the thermostat to maintain a comfortable temperature as humidity changes, including: humidity responsive circuit means having output circuit means adapted to be connected to said thermostat bridge to change the balance of said bridge as humidity changes to maintain a comfortable temperature; said humidity responsive circuit means including a capacitive element that changes in capacity with change in humidity; power supply means to energize said humidity responsive circuit means to supply said output circuit means with a signal that varies with humidity; said power supply means providing an alternating current potential to said humidity responsive circuit means to periodically charge said capacitive element; said power supply means further providing a direct current potential to said humidity responsive circuit output means to in turn provide said signal that varies with humidity; said output circuit means being so arranged and designed as to have an output range with at least one humidity value being equal to a balance value of said bridge so that said humidity responsive circuit has no effect on said thermostat at said value; and said thermostat temperature control is decreased as humidity increases, and said thermostat temperature control is increased as humidity is decreased from said balance value.

2. A humidity comfort offset circuit as described in claim 1 wherein said humidity responsive circuit means further includes a reference capacitor and diode means to minimize the effect of temperature on said humidity responsive circuit means.

3. A humidity comfort offset circuit as described in claim 2 wherein said humidity responsive circuit means further includes a filter capacitor connected to said output circuit means to limit the alternating current ripple at said output circuit means.

4. A humidity comfort offset circuit as described in claim 3 wherein said capacitive element is a polyimide capacitor.

5. A humidity comfort offset circuit as described in claim 3 wherein said humidity responsive circuit means and said power supply means are formed as an integral part of said thermostat.

6. A humidity comfort offset circuit as described in claim 3 wherein said humidity responsive circuit means, said power supply means, and said thermostat include terminal means that allow said humidity responsive circuit means to be added to said thermostat after said thermostat has initially been put into operation.

7. A humidity comfort offset circuit as described in claim 5 wherein said capacitive element is a polyimide capacitor.

8. A humidity comfort offset circuit as described in claim 6 wherein said capacitive element is a polyimide capacitor.

* * * * *